United States Patent [19]

Schneider

[11] Patent Number: 4,866,231
[45] Date of Patent: Sep. 12, 1989

[54] MICROWAVE CHAMBER FOR HEATING BIOLOGICAL MATTER

[76] Inventor: David R. Schneider, 145 S. Glenhurst, Birmingham, Mich. 48009

[21] Appl. No.: 176,611

[22] Filed: Apr. 1, 1988

[51] Int. Cl.$^4$ .............................................. H06B 6/80
[52] U.S. Cl. ......................... 219/10.55A; 219/10.55F; 128/804; 128/798
[58] Field of Search ................ 219/10.55 A, 10.55 F, 219/10.55 R, 10.55 D, 10.55 E; 128/804, 783, 798, 399

[56] References Cited

U.S. PATENT DOCUMENTS

| | | | |
|---|---|---|---|
| 1,973,911 | 9/1934 | Ruben | 128/798 |
| 2,704,802 | 3/1955 | Blass | 219/10.55 F |
| 3,263,052 | 7/1966 | Jeppson | 219/10.55 R |
| 4,197,860 | 4/1980 | Sterzer | 128/804 |
| 4,332,260 | 6/1982 | Bicher | 219/10.55 R X |
| 4,509,535 | 4/1985 | Bryan | 128/798 |
| 4,660,572 | 4/1987 | Maruyama | 219/10.55 F X |

*Primary Examiner*—Philip H. Leung
*Attorney, Agent, or Firm*—Gifford, Groh, Sheridan, Sprinkle and Dolgorukov

[57] ABSTRACT

An applicator sheath for use with a microwave energy source for controlled heating of biological matter. The sheath has a chamber lined with a metallic absorbing material to alternate energy delivered by the microwave energy source. The energy is delivered into the chamber through a leaky waveguide.

6 Claims, 2 Drawing Sheets

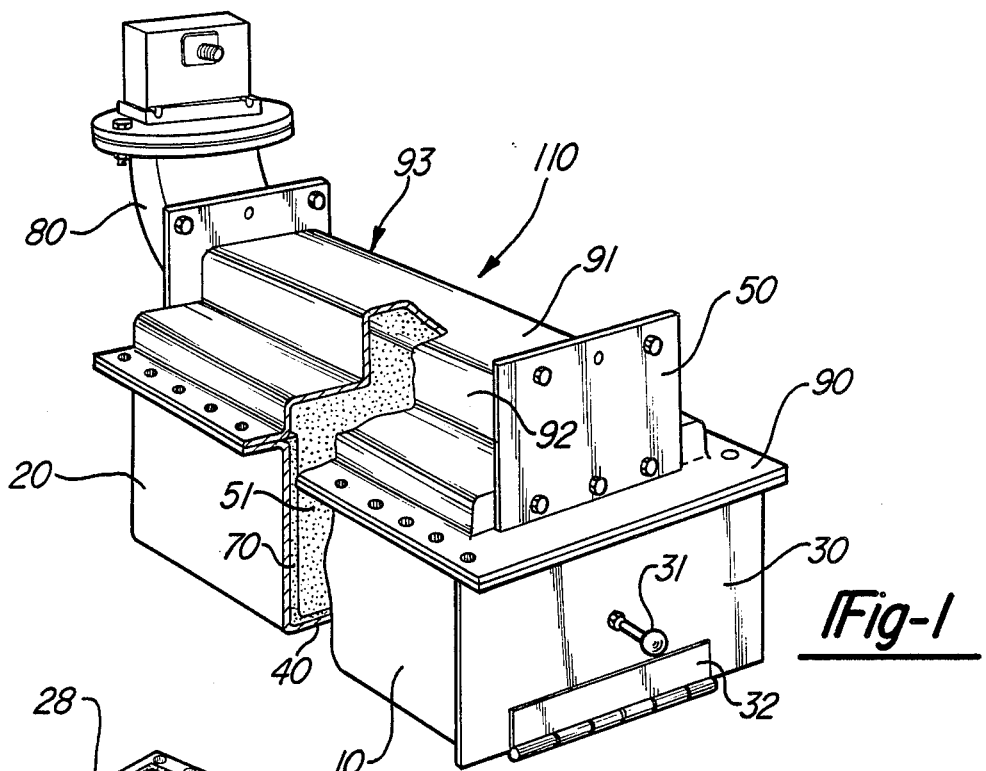
_Fig-1_
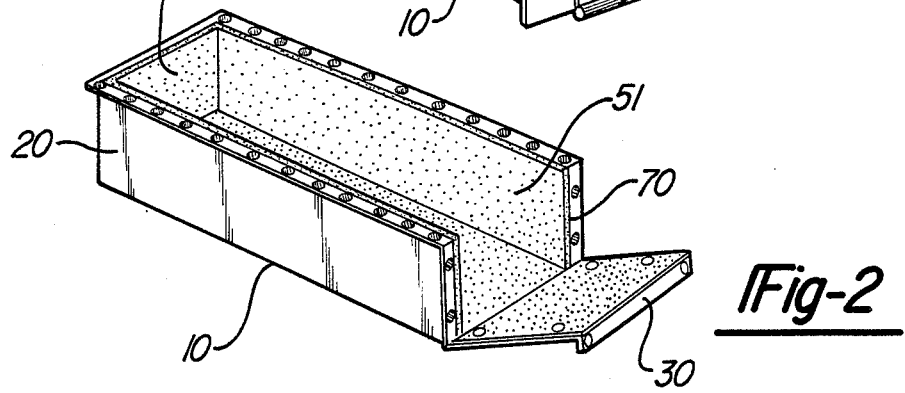
_Fig-2_
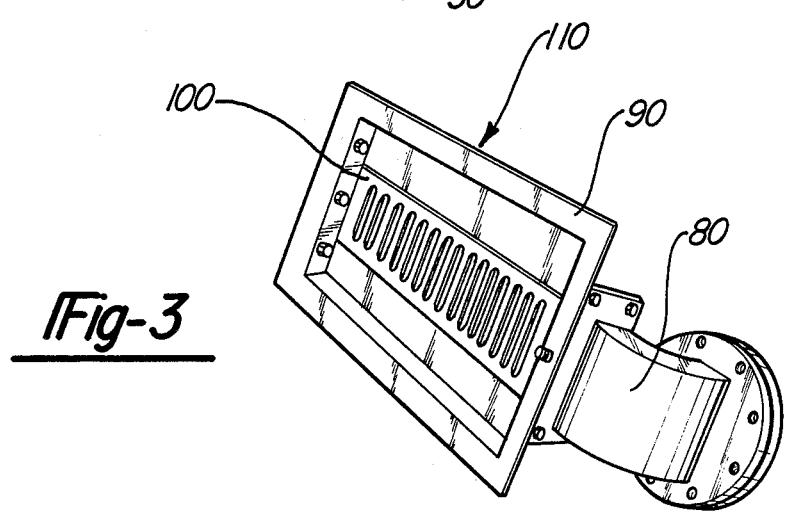
_Fig-3_

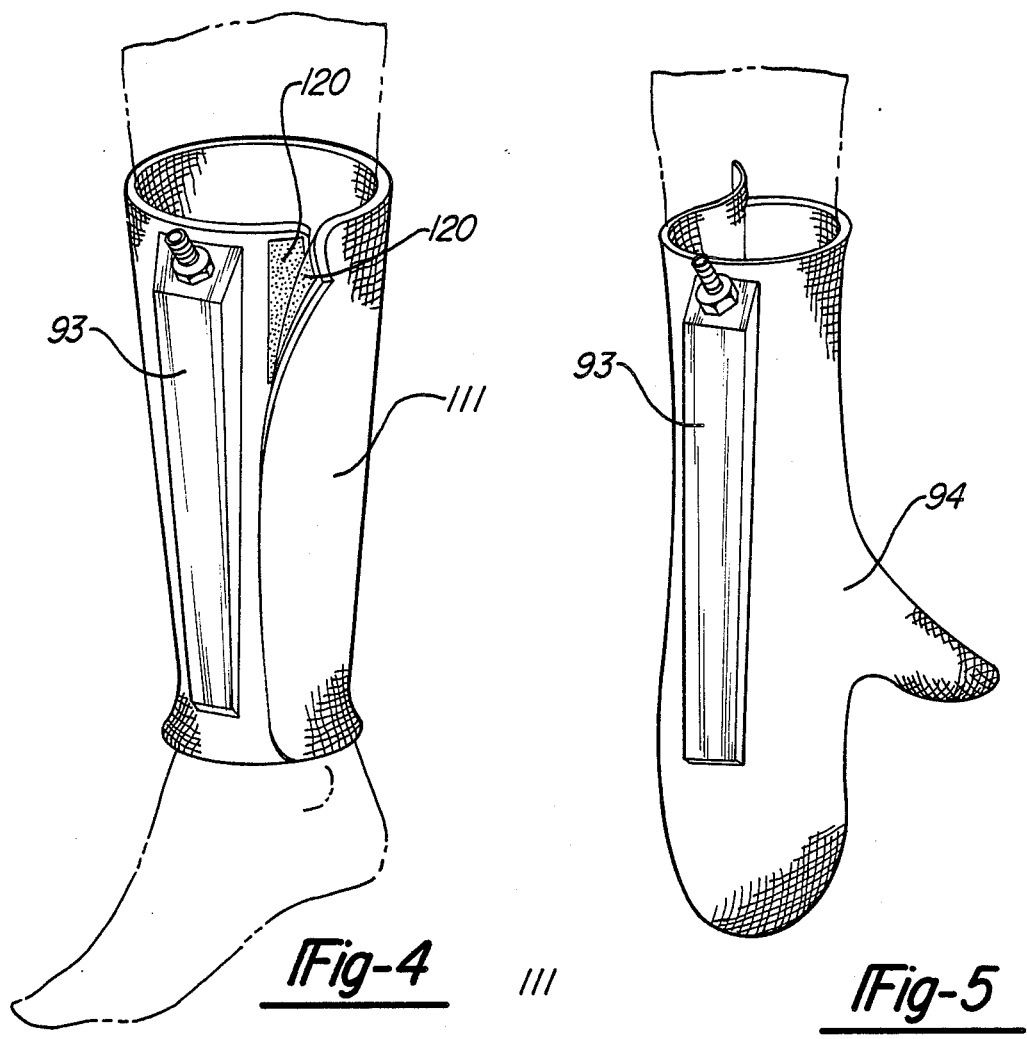
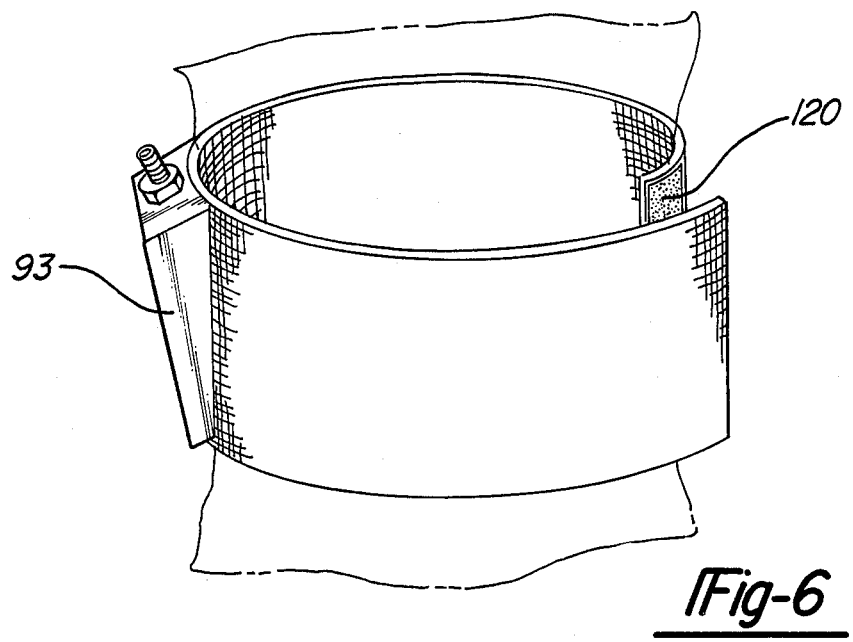

MICROWAVE CHAMBER FOR HEATING BIOLOGICAL MATTER

FIELD OF THE INVENTION

The present invention relates to a microwave applicator and chamber for heating biological matter, and more specifically to a chamber adapted for use on humans.

BACKGROUND OF THE INVENTION

Microwave energy, MWR, has been used in a variety of applications for conducting biological and medical research. In most applications, biological material is heated to an irreversible state so that examination of important biochemical substrates may be examined. More recently, the controlled application of microwave energy has been applied to biological tissues and matter in a way that does not denature or make irreversible the proteins contained in that sample.

MWR penetrates dielectric materials such as biological matter, and heats water molecules therein, turning the molecules into steam. The controlled application of MWR provides an efficient means for slightly elevating and holding the temperature of biological matter at a point above the normothermic level and beneath the temperature at which the biological matter is denatured by the steam heating of contained water.

The present invention incorporates information related to the distribution of microwave power in a process chamber as described by U.S. Pat. No. 3,263,052, entitled "Power Distribution System for Microwave Process Chambers", by Morris R. Jeppson and Franklin J. Smith. The Power Distribution System utilizes a "leaky waveguide" to provide uniform or controlled heating of the product being heated in the chamber. However, this system is not suited for use in heating biological matter because of the reflections and irregular heating patterns which are usually present within a chamber to which the leaky waveguide is attached. This is particularly true when the biological material is being heated. Therefore, it would be advantageous to have a system which could provide a uniform and controlled heating for biological matter.

SUMMARY OF THE INVENTION

The present invention provides an applicator sheath that can be coupled to the power distribution system described above and including the improvements: a sheath member defining a chamber capable of holding biological material. The sheath is provided with a lining of metallic microwave absorbing material. The sheath member is adapted with an aperture to receive a power distribution system through a leaky waveguide, said leaky waveguide being mounted within the aperture on the sheath. The applicator is also provided with an opening to receive the biological material.

As explained in detail below, the leaky waveguide is affixed to the sheath so that microwave energy being directed into said leaky waveguide will have access to the chamber enclosed therein. The leaky waveguide can be constructed in a number of configurations, the most common of which is a rectangular duct. Optimally, for the distribution of 2450 MHz energy, one would chose a rectangular waveguide measuring at least 2.84×1.41 inches i.d. Other sizes of waveguide could also be used, but might attenuate the microwave power from a generator source. For most biological applications involving human biological matter, it is important to employ only low levels of microwave energy for coupling purposes.

BRIEF DESCRIPTION OF THE DRAWINGS

An embodiment of the invention is described by way of example with reference to the accompanying drawings, in which:

FIG. 1 is representation perspective view of a sheath box containing an opening onto which a leaky waveguide is attached;

FIG. 2 is a perspective view of a sheath box chamber showing placement of microwave absorbing material placed throughout the chamber;

FIG. 3 is a perspective view of the leaky waveguide;

FIG. 4 is a perspective view of an alternative embodiment of a sheath adapted for use on a human leg;

FIG. 5 is a perspective view of an alternative embodiment of a sheath adapted for use as a mitten for the human hand; and, FIG. 6 is a perspective view of an alternative embodiment of a sheath adapted for use as a general wrapping for application to the trunk or head of a human.

DESCRIPTION OF THE PREFERRED EMBODIMENT

Generally, a leaky waveguide 110, as shown in FIG. 3, consists of a waveguide flange 90, and a broadwall containing a plurality of slotted openings 100. The waveguide 110 receives microwave energy from a source generator (not shown) through a hardware fitting 80 such as a curved waveguide duct.

As shown in FIG. 1, a sheath in the form of a box 10, having side walls 20, end walls 28 and 30, and a bottom 40 defines a chamber 51. One end wall 30 has an attached handle 31, and is mounted for opening and access to the chamber 51, by a hinge 32. The box is formed of a suitable material such as aluminum. The leaky waveguide, (FIG. 3), consists of a rectangular duct 93, formed by broad walls 91, and narrow walls 92.

The box has a flange 50, extending outwardly from the side walls and chamber. The flange permits a tight seal with the leaky waveguide, FIG. 3. The tight seal is necessary so that microwave energy does not leak from the chamber and cause hazardous conditions to an operator or to the person being treated. As shown in FIG. 2, the chamber is covered with a silicone material 70 impregnated with materials such as iron oxide which highly attenuate the magnetic field of microwave energy, said material otherwise being known under the trade name Eccosorb. The Eccosorb material acts to attenuate the energy delivered from the leaky waveguide into the the chamber so that there is an even field of energy at all points in the chamber. For optimal evenness and smoothing of the energy field within the chamber, Eccosorb must cover the back, front, both sides and the bottom of the chamber. The Eccosorb is held in place by any number of suitable techniques such as screws or glue. Eccosorb is available in several thicknesses. Satisfactory performance is achieved in a system such as that described, using a layer ⅛ inch thick. FIG. 3 shows a perspective view of the leaky waveguide, containing a waveguide flange 90, with a plurality of slotted openings in the broadwall attached to the waveguide 100. The slotted openings are placed along the broadwall of the waveguide in accordance with the pattern suggested by U.S. Pat. No. 3,263,052, cited above. The slotted openings of the leaky waveguide are located on one of the broadwall surfaces. The openings are regularly spaced, and increase in size from about 1 inch in length to approximately 2 inches in length beginning at the point where microwave energy enters the waveguide. As the openings get larger, more energy is able to be leaked from the waveguide into the chamber. The waveguide is attached to the chamber by any suitable means, such as screws or bolts.

An alternative embodiment, shown in FIG. 4, provides a sheath device adapted for use on a human limb such as a leg. A flexible metallic sheath pad 111, is held in place about the limb with fastening materials 120, such as Velcro. Along a part of the flexible metallic sheath is an opening for a waveguide 93, to be attached.

Another alternative embodiment is shown in FIG. 5, which provides a perspective view of another type 94 of sheath device, adapted for use to a human hand. The illustration shows a flexible metallic sheath 111 to which is attached a waveguide flange 93.

FIG. 6 provides a perspective view of a wrapping suitable for use on the trunk of the human body. The wrapper illustrates use of a flexible metallic sheath 111, with a fastening material 120, and an opening containing a waveguide flange 93.

In practice, the invention is used by placing biological matter into the sheath through the access opening. The chamber is then sealed, and microwave power through the leaky waveguide is applied into the chamber and into the biological matter. Within the chamber the specimen is then evenly heated in a controlled manner.

The present invention is not limited to the particular embodiments which have been described above, but extend to any variant thereof lying within the scope of the claims. For example, the leaky waveguide can functionally be split so that more than one waveguide could be present on a given sheath. In such a configuration there would be more than one access opening into the chamber from the sheath.

Further, it is also important to recognize that circularly polarized microwave energy could be employed if required. Circularly polarized energy would require two generator sources which would feed 90° phase shifted signals to a circular waveguide attached to the sheath.

In addition, microwave energy at frequencies other than 2450 MHz could also be very useful and applicable to the device described by this invention. A useful energy source might deliver energy in the 900 MHz range; another energy source could deliver energy in the 5000 MHz range for applications requiring the coupling of energy to biological matter. Energy in the 900 MHz range could be delivered through standard components, including coaxial transmission lines and coupling arrangements. Similar hardware is available for producing and delivering energy in the 5000 MHz range. One advantage of using energy in the 900 MHz range or the 5000 MHz range over a standard 2450 MHz energy source would be in th depth of penetration into the biological matter which could be achieved by these other frequencies. While 2450 MHz energy penetrates most biological matter (depending on the dielectric constant of the biological matter) to an average depth of 1-1.5 cm, energy in the 900 MHz range would penetrate further (to 4 cm), while energy in the 5000 MHz range would penetrate only a few millimeters into the biological matter.

We claim:

1. An apparatus for heating biological material through microwave radiation, said apparatus comprising:
   a sheath member having an outer surface and an inner surface, said inner surface defining a chamber adapted for accepting biological matter, said sheath member having an aperture;
   a leaky waveguide mounted to said sheath for directing radiation through said aperture into said chamber to directly contact said biological matter;
   means for access to said chamber for insertion and removal of said biological matter; and
   a layer of silicone material impregnated with attenuation material mounted to said inner surface of said sheath member, said layer of silicone material covering said inner surface whereby energy from said radiation directed by said leaky waveguide is attenuated to form an even field of energy throughout said chamber for controllably heating said biological matter.

2. The apparatus of claim 1, wherein said sheath member comprises a box having a pair of sides and a pair of ends defining a top aperture, said leaky waveguide being mounted in said top aperture.

3. The apparatus of claim 2 wherein said means for access comprises a door movably mounted at one of said pair of ends.

4. The apparatus of claim 3, wherein said sheath member comprises a flexible pad having a pair of edges, said means for access comprises a means for fastening affixed to said pair of edges.

5. The apparatus of claim 1, wherein said sheath member comprises a pad member having the shape of a human hand, and defining a chamber within for accepting said hand.

6. The apparatus of claim 1, wherein said sheath member comprises a pad member having the shape of a human foot, and defining a chamber within for accepting said foot.

* * * * *